United States Patent [19]

Ritter et al.

[11] Patent Number: 5,210,281
[45] Date of Patent: May 11, 1993

[54] DRY NEUTRALIZATION PROCESS FOR ORGANIC LIQUID PHASES

[75] Inventors: Wolfgang Ritter, Haan; Hans-Dieter Sitz, Rommerskirchen; Ludwig Speitkamp, Duesseldorf, all of Fed. Rep. of Germany

[73] Assignee: Henkel Kommanditgesellschaft auf Aktien, Duesseldorf-Holthausen, Fed. Rep. of Germany

[21] Appl. No.: 720,444

[22] PCT Filed: Dec. 15, 1989

[86] PCT No.: PCT/EP89/01547
§ 371 Date: Aug. 23, 1991
§ 102(e) Date: Aug. 23, 1991

[87] PCT Pub. No.: WO90/07484
PCT Pub. Date: Jul. 12, 1990

[30] Foreign Application Priority Data

Dec. 24, 1988 [DE] Fed. Rep. of Germany ....... 3843843
Nov. 27, 1989 [DE] Fed. Rep. of Germany ....... 3939163

[51] Int. Cl.$^5$ .............................................. C07C 67/48
[52] U.S. Cl. .................................................. 560/218
[58] Field of Search ........................................ 560/218

[56] References Cited

U.S. PATENT DOCUMENTS 4,304,925 12/1981 Watanabe .......................... 560/218

Primary Examiner—Paul J. Killos
Attorney, Agent, or Firm—Ernest G. Szoke; Wayne C. Jaeschke; Daniel S. Ortiz

[57] ABSTRACT

The invention relates to a process for the production of pure, substantially neutral, low-volatility organic compounds containing reactive olefinic double bonds from starting materials which contain these components together with small quantities of acidic reaction constituents and/or corresponding auxiliaries in the liquid phase by neutralization and separation of the salts formed. The process according to the invention is characterized in that, to obtain pure products which combine low residual acid values with low color standard numbers, even without distillation, the neutralization is carried out as dry neutralization using solid, finely powdered oxides, carbonates and/or hydroxides of the alkali and/or alkaline earth metals, if desired together with other insoluble basic metal oxide compounds, and the organic liquid phase is subsequently separated from the finely powdered solid phase. The oxides and/or hydroxides of calcium and/or magnesium are preferably used for neutralization.

17 Claims, No Drawings

DRY NEUTRALIZATION PROCESS FOR ORGANIC LIQUID PHASES

This invention relates to an improved process for the production of pure, substantially neutral, low-volatility organic components containing reactive olefinic double bonds which are susceptible to polymerization or gelation. More particularly, the invention seeks to provide an improved processed for the production of pure, low-volatility organic components of the type mentioned which are difficult or impossible to purify by distillation.

The problem addressed by the present invention is described hereinafter with reference by way of example to a selected class of compounds which may be produced with particular advantage using the measures proposed in accordance with the invention. However, the expert will readily appreciate that the invention is not limited in its scope to this particular class of compounds. The new measures proposed in accordance with the invention may be applied in any fields of application where comparable, technologically created or freely selected problems have to be solved.

It is known that low-volatility polyfunctional esters of acrylic acid and/or methacrylic acid with polyhydric alcohols — hereinafter also referred to as (meth)acrylates or multifunctional (meth)acrylates — can be produced by reaction of the reactants in the presence of acidic esterification catalysts with addition of polymerization inhibitors to the reaction mixture. (Meth)acrylates of this type are acquiring increasing significance as highly reactive constituents of, for example, radiation-curing systems. The polyfunctional alcohols on which these esters are based are, for example, dihydric to tetrahydric aliphatic, saturated alcohols and/or alkoxylation products thereof. Polyfunctional (meth)acrylates of the type mentioned may be used, for example, as paint resins for curing by electron beams or as a constituent of UV-curing printing inks or corresponding coating compositions, in surfacing compositions, molding or encapsulating compounds and in adhesives, particularly anaerobic adhesives. However, their production is not without problems. The products required should be, above all, substantially colorless and odorless with a low acid value and high stability in storage. (Meth)acrylates of the type in question here generally cannot be purified by distillation on account of their high molecular weight and their high reactivity. The solvent-containing or solvent-free mixtures obtained as the crude reaction products may contain the acidic catalyst and possibly even acid residues from the esterification reaction, i.e. have to be subjected to neutralization and purification to bring the non-distilled product to the required quality.

The present invention is based on the concept of carrying out this concluding neutralization and purification step as so-called dry neutralization. Dry neutralization is understood to be the procedure in which an at least substantially dry, basic neutralizing agent is added to the organic crude reaction product in the form of a fluid paste, at least in the substantial absence and preferably in the complete absence of water, to bind the acidic components (catalyst, residual acids and the like), after which the added solid phase is separated from the fluid organic phase after the desired residual acid value has been established.

However, during the development of an industrial process based on this concept, it was found that the requirements stipulated to satisfy because, where selected process conditions are specifically varied to optimize a desired product property, for example the low acid value, other product properties, for example the color and/or stability of the reaction product, are adversely affected. The various problems involved are illustrated by way of example in the following: highly reactive (meth)acrylate systems of the type in question tend to gel through anionic polymerization on the addition of finely divided, solid, basic neutralizing agents. The desired neutralization of the acidic components present in the reaction mixture becomes preferential reaction over the anionic gelation if the reaction temperature is increased to high levels. However, elevated temperatures in turn adversely affect the residual color value of the neutralized product.

The invention starts out from this mutually impeding linking of the desired and adjustable product properties. The teaching according to the invention shows how end products having the desired high-level qualification over the entire property spectrum can be obtained despite there impediments.

Accordingly, the present invention relates to a process for the production of pure, substantially neutral, low-volatility organic compounds containing reactive olefinic double bonds from starting materials which contain these components together with small quantities of acidic reaction constituents and/or corresponding auxiliaries in the liquid phase by neutralization and separation of the salts formed. The process according to the invention is characterized in that, to obtain pure products which combine low residual acid values with low color standard numbers, even without distillation, the neutralization is carried out as dry neutralization using solid, finely powdered oxides, carbonates and/or hydroxides of the alkali and/or alkaline earth metals and the organic liquid phase is subsequently separated from the finely powdered solid phase. The oxides and/or hydroxides of the alkaline earth metals may be used as such for the dry neutralization although, in one particular embodiment of the invention, they may even be used together with other insoluble, basic metal oxide compounds.

Particular significance is attributed to the use of finely divided, more especially finely powdered, oxides and/or hydroxides of calcium and/or magnesium for carrying out the dry neutralization. Of these two alkaline earth metals, particular significance is attributed to the corresponding compounds of calcium. In one preferred embodiments of the invention, finely divided solids at least partly containing calcium compounds of the type mentioned are introduced into the dry neutralization stage. One particularly important embodiment is characterized by the use of calcium hydroxide $Ca(OH)_2$ and/or quicklime CaO. Finely divided calcium hydroxide in particular often provides for an optimal balance between the mutually conflicting process parameters of residual acid value, color standard number, thermal stress capacity, process time, quantity of dry neutralizing agent used and the like.

Another important parameter, which has not yet been discussed in the disclosure of the invention, is the possible interaction between the dry neutralizing agent used and the polymerization inhibitors normally used in systems of the type in question. In this case, too, interactions are possible, although not essential, on account of the special structure of the particular inhibitor or inhibitor system present in the one hand and the solid neutralizing agent used on the other hand. Particulars in this regard can be found in applicants' co-pending, patent application Ser. No. 07/859,429 filed 24 Sep. 1992. "A process for inhibitor exchange in radical-reactive olefinically unsaturated systems". In applying the technical teaching described in the disclosure of the present invention, the expert will have to consider from case to case to what extent inhibition of the dry-neutralized reaction product is guaranteed after separation of the solid phase. The inhibitor content of the purified reaction product may have to be adjusted to the predetermined value by the addition of more inhibitor. Basically, inhibitors belonging to the typical classes of compound in question here for inhibiting unwanted radical initiation of polymerization also interact with the dry neutralizing agents to a more or less high degree and may be removed, generally in parts, from the reaction mixture via the dry neutralizing agents. Depending on the requirements which the end product has to satisfy in regard to inhibition, it may then be advisable or even necessary to replace those parts of the radical inhibitors which have been removed.

Another crucial process parameter for the optimization according to the invention is the choice of the temperature range for the dry neutralization process. Even the solid systems selected in accordance with the invention on the basis of the oxides and/or hydroxides of the alkaline earth metals, particularly magnesium and/or calcium, can lead to the initiation of an anionic polymerization and hence to gelation of the reaction product in the case of comparatively highly reactive, olefinically unsaturated systems either at room temperature or even at slightly elevated temperature. According to the invention, therefore, it is preferred to carry out the dry neutralization at temperatures above 50° C., the range from about 60° to 100° C. and, above all, the range from about 70° to 90° C. having proved to be a particularly interesting temperature range. Temperatures in this range promote the salt-forming neutralization over the initiation of anionic polymerization. However, this increase in temperature considerably increases the danger of the reaction product undesirably darkening in color.

These problems are overcome on the one hand by the restricted choice of the dry neutralizing agents made in accordance with the invention. The color of the reaction product may also be influenced by the choice of the duration of the neutralizing treatment. The following observations apply in this regard:

The dry neutralization according to the invention takes place slowly by comparison with salt formation from ion solutions. This delay in neutralization is additionally promoted by two factors to be taken account here: both for reasons of economy and for reasons of optimal protection of the basically labile reaction mixture, the solid basic neutralizing agent is preferably used in only a limited stoichiometric excess. The adequate residence time of the neutralizing agent in suspension in the liquid starting material must therefore be long enough to ensure adequate contact between solid and liquid or rather dissolved reactants. In addition, the outer surface of the individual solid particles becomes covered comparatively quickly with the particular salt formed, thus impeding the deeper penetration of the acidic components to be neutralized into the core of the solid particle.

The dry neutralization process according to the invention may be carried out over a period of a few hours, for example up to 3 hours and preferably up to 1 to 2 hours. However, to achieve the optimization which the process according to the invention seeks to provide, it may be appropriate to adapt the process temperature and process time to one another in such a way that a treatment time of less than 1 hour and, in particular, less than 45 minutes is sufficient for adjusting the low residual acid values required. In particularly preferred embodiments, the working conditions are adapted to one another in such a way that residual acid values below 1 mg KOH/g substance are obtained over a period of up to about 30 minutes and preferably over a period of from about 5 to 30 minutes. Where calcium hydroxide is used as the dry neutralizing agent, optimal values can generally be adjusted over a treatment time of from about 5 to 60 minutes at a temperature of the order or 80° C. According to the invention, it is thus possible to establish the low residual acid value required of, preferably, approximately 0.5 mg KOH/g substance or even lower, but at the same time to keep the color standard numbers of the non-distilled material below 2 and preferably at about 1. The color standard numbers are determined by the GARDNER method.

Particular significance may be attributed to the following parameter of the process according to the invention, particularly for the development of color standard number in the end product:

It has been found that the presence of water in the reaction product to be treated can adversely affect the development of the color standard number to be established. Even comparatively small quantities of aqueous base solutions of the type in question here apparently have a more discoloring effect under the otherwise optimized process conditions than the dry neutralizing agent in solid form. According to the invention, therefore, it is preferred that the material to be neutralized and to be used as the liquid phase be initially introduced in at least substantially anhydrous form. Any residues of water present in the material to be purified may be removed in known matter, for example using auxiliary solvents by azeotropic distillation or simply be applying vacuum for a sufficiently long period of time.

In one particular embodiment of the invention, however, the same notion is developed along the following lines: it has proved to be appropriate to carry out the neutralization reaction at least partly under reduced pressure, even when the liquid to be neutralized is basically anhydrous. Where neutralization is carried out under reduced pressure, the water formed during neutralization is also removed from the reaction mixture so that the in situ formation of aqueous basic solutions during neutralization is prevented or at least restricted. It can be appropriate in this regard to carry out neutralization under a pressure in the range from about 1 to 150 mbar, for example at a pressure in the range from about 20 to 150 bar, pressures in the range from about 20 to 100 mbar being particularly preferred. It is possible in this way to reduce residual water contents in the end product to levels below about 0.1% by weight whereas, in the dry neutralization of standard crude products, residual water contents of from about 0.7 to 0.9% by weight can be present on completion of neutralization in the absence of vacuum on account of the presence of free acid components in the crude products. It has been found that even these relatively high residual water contents can bring about substantial deteriorations in the color standard number of the purified end product.

The quantity of finely powdered basic auxiliary added in the neutralization stage is primarily determined by the total quantity of free acid components to be neutralized in the crude product. The finely powdered neutralizing agents are preferably added in an at least substantially stoichiometric quantity. In general, it may be appropriate to use a limited excess of the solid neutralizing agent. In general, the excess will not exceed about 2.5 to 3 times the stoichiometrically necessary quantity, again based on the total acid present. It can be particular advantage to use the base in quantities of about 1.3 to 2 times the stoichiometrically necessary quantity.

It has been found that individual significance can be attributed to the components intended for neutralization in accordance with the invention in the "fine tuning" of the particular effects they initiate. Powder-form calcium hydroxide very effectively reduces the residual acid value and can also lead to low color standard numbers. However, low color standard numbers are only guaranteed when the contact time of the reaction mixture with the calcium hydroxide is kept comparatively short. As already mentioned, optimal results can be obtained in this regard by working at temperatures of the order of 80° C. over a period of from about 10 to 30 minutes. Calcium hydroxide also has a comparatively strong effect in regard to the residues of polymerization inhibitor remaining in the reaction mixture providing there is sufficient reactivity between the inhibitor and the calcium hydroxide. By contrast, the quicklime is a good neutralizing agent which unfortunately shows comparatively weak interaction with inhibitors basically capable of salt formation. The combination of magnesium and calcium compounds of the type mentioned can lead to improved color standard numbers coupled with an adequate neutralizing effect. This may also be accompanied by a comparatively weak interaction with inhibitors capable of salt formation.

As mentioned at the beginning, the alkaline earth oxides or hydroxides selected in accordance with the invention may also be used in admixture with other basic metal oxides or metal oxide compounds capable of salt formation. A particularly interesting example in this regard is hydrotalcite. Combinations of hydrotalcite and basic calcium compounds of the type mentioned lead to particularly good color values in the end product coupled with effective lowering of the residual acid value.

Hydrotalcites are mixed hydroxide compounds having an inorganic basic structure which can be produced in finely divided, insoluble form and which represent two-dimensional inorganic polycations with inner-crystalline charge equalization by labile inter-layer anions. They are also known as "double-layer hydroxides" and have been repeatedly described in the literature, cf. for example R. Allmann "Doppelschichtstrukturen mit brucitähnlichen Schichtionen...", Chimia 24, 99 to 108 (1970). Various possible methods for the large-scale production of these compounds are described in DE-OS 20 61 156. A well-characterized representative of this group of compounds is hydrotalcite which occurs in nature as a mineral and which may also be synthetically produced. Hydrotalcite is a magnesium-aluminium hydroxocarbonate having the approximate composition $Mg_6Al_2(OH)_{16}$—$CO_3 \times 4\ H_2O$, cf. R. Allmann et al. "Die Struktur des Hydrotalkits", N. Jahrb. Mineral. Monatsh. 1969, 544 to 551.

The following Examples describe the effect of various dry neutralizing agents according to the invention, the individual effects they produce on variation of the process parameters and optimal result combinations where the various elements determining the process according to the invention are suitably coordinated in accordance with the teaching of the invention.

EXAMPLES

Example 1

800 g of a crude esterification product consisting of 28 g toluenesulfonic acid, 1.6 g 2,5-di-tert.-butyl hydroquinone, 30.8 g acrylic acid and 739.6 g trimethylol propane + 3 EO triacrylate were weighted into a 1 liter flask. The crude product was neutralized with stirring at temperatures of 80° to 40° C. while air was passed through at 10 l/h. Twice the equivalent quantity of base, based on the acid value of the crude product (acid value: 40 mg KOH/g substance), were used for neutralization.

Quantities of approximately 200 g of the neutralized product were removed after 1, 2, 3 and 24 hours and filtered by a pressure nutsche. The results obtained in regard to the acid values of the products are shown in Table 1.

Only with bases which produced acid values of less than or equal to 6 mg KOH/g at a neutralization temperature of 80° C. was the temperature reduced to 60° C. The bases which then led to acid values of less than or equal to 6 mg KOH/g were also used for neutralization at 40° C.

TABLE 1

Screening of the neutralization substances in regard to acid value
Starting product: trimethylol propane + 3 EO triacrylate (acid value: 40 mg KOH/g substances)

| Base | Neutralization: 2x equimolar; 80° C. | | | | Neutralization: 2x equimolar; 60° C. | | | | Neutralization: 2x equimolar; 40° C. | | | |
|---|---|---|---|---|---|---|---|---|---|---|---|---|
| | 1 h mg/g | 2 h mg/g | 3 h mg/g | 1 d mg/g | 1 h mg/g | 2 h mg/g | 3 h mg/g | 1 d mg/g | 1 h mg/g | 2 h mg/g | 3 h mg/g | 1 d mg/g |
| $Li_2CO_3$ (MW: 73.9) | | | | | | | | | | | | |
| LiOH (MW: 24.0) | 9.8 | 2.2 | 1.3 | 1.3 | 17.6 | 14.3 | 10.5 | 9.2 | | | | |
| $Na_2CO_3$ (MW: 106.0) | 4.6 | — | 0.4 | 2.6 | 2.5 | 1.2 | 0.4 | 0.2 | 29.3 | 25.6 | 7.8 | gelation |
| $NaHCO_3$ (MW: 84.0) | 31.6 | 26.2 | 23.7 | 27.1 | | | | | | | | |
| NaOH fine (MW: 40.0) | 25.8 | 5.0 | 2.8 | 2.4 | 9.4 | 0.7 | 0.4 | 0.2 gelation | 35.7 | 29.8 | 27.3 | 25.5 gelation |
| NaOH coarse (MW: 40.0) | 38.4 | 36.4 | 33.2 | 34.2 | | | | | | | | |

TABLE 1-continued

Screening of the neutralization substances in regard to acid value
Starting product: trimethylol propane + 3 EO triacrylate (acid value: 40 mg KOH/g substances)

| | Neutralization: 2x equimolar; 80° C. | | | | Neutralization: 2x equimolar; 60° C. | | | | Neutralization: 2x equimolar; 40° C. | | | |
|---|---|---|---|---|---|---|---|---|---|---|---|---|
| Base | 1 h mg/g | 2 h mg/g | 3 h mg/g | 1 d mg/g | 1 h mg/g | 2 h mg/g | 3 h mg/g | 1 d mg/g | 1 h mg/g | 2 h mg/g | 3 h mg/g | 1 d mg/g |
| $K_2CO_3$ (MW: 138.2) | 6.7 | 2.1 | 0.7 | 1.1 | 7.9 | 1.9 | 0.2 | 0.5 | 10.3 | 7.9 | 1.9 | gelation |
| $KHCO_3$ (MW: 100.1) | | | | | | | | | | | | |
| KOH fine (MW: 56.1) | 39.1 | 29.6 | 24.4 | 22.3 | | | | | | | | |
| KOH coarse (MW: 56.1) | 38.7 | 37.9 | 35.8 | 36.2 | | | | | | | | |
| $(MgCO_3)_4 \times Mg(OH)_2 \times 5H_2O$ (MW: 485.7) | 27.9 | 24.6 | 25.3 | 29.0 | | | | | | | | |
| $Mg(OH)_2$ (MW: 58.3) | 15.1 | 10.9 | 8.5 | 14.4 | 30.0 | 28.7 | 26.3 | 26.5 | | | | |
| MgO (MW: 40.3) | 5.8 | 5.6 | 3.1 | 5.7 | 11.3 | 10.1 | 7.4 | 10.0 | | | | |
| $CaCO_3$ (MW: 100.0) | 29.3 | 27.8 | 26.4 | 29.0 | | | | | | | | |
| $Ca(OH)_2$ (MW: 74.1) | 0.9 | 0.2 | 0.1 | 0.3 | 5.1 | 0.7 | 0.3 | 0.5 | 4.2 | gelation | | |
| CaO (MW: 56.1) | 23.6 | 8.4 | 3.2 | 0.6 | 23.6 | 17.7 | 12.9 | 9.0 | | | | |
| $Al_2O_3$ (MW: 102.0) | 39.7 | 39.7 | 37.4 | 37.2 | | | | | | | | |
| $Al(OH)_3$ (MW: 78.0) | 39.8 | 37.8 | 36.5 | 40.2 | | | | | | | | |
| Hydrotalcite | 7.7 | 6.8 | 5.6 | 6.1 | 18.9 | 17.3 | 15.0 | 15.6 | | | | |

EXAMPLE 2

1.5 kg of a crude esterification product (52.5 g p-toluene sulfonic acid, 3.0 g 2,5-di-tert.-butyl hydroquinone, 53.9 g acrylic acid and 1390.6 g trimethylol propane + 3 EO triacrylate, OH value 34 mg KOH/g, acid value 38 mg KOH/g, Gardner color standard number 1, $H_2O$ content 0.40% by weight) were weighed into a 2 liter reactor and neutralized with 48.9 g $Ca(OH)_2$ at 80° C. while air was passed through at 20 l/h. After a neutralization time of 1, 2 and 3 hours, one third of the quantity of product was removed and filtered by a pressure nutsche. Neutralization was then carried out on the one hand at normal pressure and, on the other hand, in a vacuum of 50 mbar to eliminate residues of water. The results are shown in Table 2.

TABLE 2

Dependence of the product specifications on the pressure prevailing during neutralization Starting product: trimethylol propane + 3 EO triacrylate
Acid value: 38 mg KOH/g
Hydroxyl value: 34 mg KOH/g
Gardner color standard number: 1
Water content: 0.40% by weight

| Temperature 80° C. | Neutralization time h | Acid value mg KOH/g | Hydroxyl value mg KOH/g | Gardner color standard number | Water content % by weight |
|---|---|---|---|---|---|
| 48.9 g $Ca(OH)_2$ Normal pressure | 1 | 2.9 | 50 | below 1 | 0.90 |
| | 2 | 0 | 51 | 2 | 0.83 |
| | 3 | 0 | 51 | 3 | 0.61 |
| 48.9 g $Ca(OH)_2$ 50 mbar | 1 | 7.1 | 47 | below 1 | 0.06 |
| | 2 | 4.1 | 47 | below 1 | 0.10 |
| | 3 | 2.0 | 48 | below 1 | 0.02 |

EXAMPLE 3

1.0 kg of an esterification product (as in Example 2) was weighed into a 2-liter reactor and neutralized at a temperature of 80° C. under a pressure of 50 mbar while air was passed through at 20 l/h. The quantities of neutralizing agents were as follows:

$Ca(OH)_2$ 26.2 g; 32.5 g; 34.5 g; 37.5 g; 39.9 g; 49.9 g
CaO 28.4 g; 37.8 g

After a neutralization time of 1, 2 and 3 hours one third of the product was removed and filtered by a pressure nutsche. The results obtained in regard to acid value, OH value and color standard number are shown in Table 3.

TABLE 3

Dependence of the product specifications on the quantity of neutralizing agent

Starting product: trimethylol propane + 3 EO triacrylate
Acid value: 38 mg KOH/g
Hydroxyl value: 34 mg KOH/g
Gardner color standard number: 1
Water content: 0.40% by weight

| Temperature: 80° C. Pressure: 50 mbar | Neutralization time h | Acid value mg KOH/g | Hydroxyl value mg KOH/g | Gardner color standard number |
|---|---|---|---|---|
| 26.2 g $Ca(OH)_2$ 1x equival. | 1 | 9.2 | 39.7 | below 1 |
| | 2 | 6.7 | 42.8 | below 1 |
| | 3 | 5.7 | 48.8 | below 1 |
| 32.5 g $Ca(OH)_2$ 1.3x equival. | 1 | 7.1 | 47 | below 1 |
| | 2 | 4.1 | 47 | below 1 |
| | 3 | 2.0 | 48 | below 1 |
| 34.5 g $Ca(OH)_2$ 1.4x equival. | 1 | 5.1 | 50 | below 1 |
| | 2 | 2.6 | 50 | below 1 |
| | 3 | 0.2 | 50 | 2 |
| 37.5 g $Ca(OH)_2$ 1.4x equival. | 1 | 2.7 | 45 | below 1 |
| | 2 | 1.5 | 45 | 1 |
| | 3 | 0.4 | 53 | 2 |
| 39.9 g $Ca(OH_2)$ | 1 | 2.9 | 46 | 1 |

TABLE 3-continued

Dependence of the product specifications on the quantity of neutralizing agent

| | | | | |
|---|---|---|---|---|
| 1.6x equival. | 2 | 0 | 46 | 3 |
| | 3 | 0 | 49 | 4 |
| 49.9 g Ca(OH)$_2$ | 1 | 0 | 48 | 1 |
| 2x equival. | 2 | 0 | 51 | 2 |
| | 3 | 0 | 54 | 3 |
| 28.4 g CaO | 1 | 11.4 | 43 | below 1 |
| 1.5x equival. | 2 | 6.5 | 44 | below 1 |
| | 3 | 4.8 | 46 | below 1 |
| 28.4 g CaO | 1 | 3.9 | 44 | below 1 |
| 2x equival. | 2 | 1.7 | 49 | 1-2 |
| | 3 | 0.1 | 49 | 1-2 |

EXAMPLE 4

1.8 kg of an esterification product (as in Example 2) were weighed into a 2-liter reaction and neutralized with 90.3 g Ca(OH)$_2$ at 80° C. under a pressure of 50 mbar while air was passed through at 20 l/h. Quantities of approximately 200 g of product were removed after 10, 20, 30, 40, 50, 60, 120, 180 and 1440 minutes and filtered by a pressure nutsche. The results obtained in regard to acid value, hydroxyl value and color standard numbers are shown in Table 4.

TABLE 4

Dependence of the product specifications on the neutralization time

Starting product: trimethylol propane + 3 EO triacrylate
Acid value: 38 mg KOH/g
Hydroxyl value: 34 mg KOH/g
Gardner color standard number: 1
Water content: 0.40% by weight

| Temperature: 80° C. Pressure: 50 mbar | Neutralization time mins | Acid value mg KOH/g | Hydroxyl value mg KOH/g | Gardner color standard number |
|---|---|---|---|---|
| 90.3 g Ca(OH)$_2$ | 10 | 0.3 | 39 | below 1 |
| 2x equival. | 20 | 0 | 42 | below 1 |
| | 30 | 0 | 45 | below 1 |
| | 40 | 0 | 47 | below 1 |
| | 50 | 0 | 47 | 1 |
| | 60 | 0 | 48 | 1 |
| | 120 | 0 | 51 | 2 |
| | 180 | 0 | 54 | 3 |
| | 1440 | 0 | 58 | 4 |

EXAMPLE 5

1.0 kg of an esterification product (35 g p-toluene sulfonic acid; 2 g 2,5-di-tert.-butyl hydroquinone; 38.5 g acrylic acid, 94.5 g neopentyl glycol + 2 PO diacrylate; hydroxyl value: 20 mg KOH/g, acid value 40 mg KOH/g, Gardner color standard number 1) were weighed into a 2-liter reactor and neutralized at 80° C. under a pressure of 50 mbar while air was passed through at 20 l/h. The neutralizing agents were mixtures or combinations of relatively mildly basic and relatively strongly basic substances.

Mixtures (1:1 equivalent):
a) 10.2 g MgO
   18.7 g Ca(OH)$_2$     (1.5x equivalent, based on the acid value of the crude product)
b) 17.8 g of hydrotalcite
   19.7 g Ca(OH)$_2$     (1.5x equivalent, based on the acid value of the crude product)

Combinations:
a) 28.5 g MgO 60 mins    (2x equivalent, based on the acid value of the crude product)
   +20. g Ca(OH)$_2$ 120 mins    (1.5x equivalent, based on the acid value after 60 mins)
b) 47.5 g hydrotalcite 60 mins    (2x equivalent, based on the acid value of the crude product)
   +8.0 g Ca(OH)$_2$ 120 mins    (1.5x equivalent, based on the acid value after 60 mins).

One third of the product was removed after 60, 120 and 180 minutes and filtered by pressure nutsche. The results obtained in regard to acid value, hydroxyl value and color standard number are shown in Table 5.

TABLE 5

Dependence of the product specifications where mixtures and combinations of neutralization substances are used Starting product: neopentyl glycol + 2 PO diacrylate
Acid value: 40 mg KOH/g
Hydroxyl value: 20 mg KOH/g
Gardner color standard number: 1

| Temperature: 80° C. Pressure: 50 mbar | Neutralization time mins | Acid value mg KOH/g | Hydroxyl value mg KOH/g | Gardner color standard number |
|---|---|---|---|---|
| Mixture: | | | | |
| 1:1 equival. | 60 | 3.7 | 36 | below 1 |
| 18.7 g Ca(OH)$_2$ | | | | |
| 10.2 g MgO | 120 | 1.9 | 38 | below 1 |
| (1.5x equival.) | 180 | 1.6 | 42 | below 1 |
| Mixture: | | | | |
| 1:1 equival. | 60 | 4.2 | 35 | below 1 |
| 19.7 g Ca(OH)$_2$ | | | | |
| 17.8 g hydrotalcite | 120 | 2.8 | 35 | below 1 |
| (1.5x equival.) | 180 | 1.9 | 39 | below 1 |
| Combination | | | | |
| 28.5 g MgO | 60 | 20.2 | 31 | below 1 |
| (2x equival., based on AV) | | | | |
| +20 g Ca(OH)$_2$ | 120 | 0.7 | 37 | below 1 |
| (1.5x equival., based on AV after 60 mins) | 180 | 0.3 | 40 | below 1 |
| Combination | | | | |
| 47.5 g hydrotalcite (2x equival., based on AV | 60 | 8.1 | 35 | below 1 |
| | 120 | 1.4 | 37 | below 1 |
| +8.0 g Ca(OH)$_2$ (1.5x equival., based on AV after 60 mins) | 180 | 0.8 | 40 | below 1 |

EXAMPLE 6

1551.7 g of an esterification product consisting of 43.4 g p-toluene sulfonic acid, 2.5 g 2,5-di-tert.-butyl hydroquinone, 36.5 acrylic acid, 1119.1 g trimethylol propane + 3 EO triacrylate and 350.2 g toluene (acid value: 18. mg KOH/g; hydroxyl value 25.3 mg KOH/g; Gardner color standard number: below 1) were weighed into a 2-liter reactor.

The neutralization was carried out at 80° C. and normal pressure. 36.9 g Ca(OH)$_2$; 27.9 g CaO and combinations of 20.1 g MgO (60 mins.)+28.9 g Ca(OH)$_2$ (120 mins.) and 25.6 g hydrotalcite (60 mins.)+19.9 g Ca(OH)$_2$ (120 mins.) were used as neutralizing agents. One third of the product was removed after 1, 2 and 3 hours and filtered by a pressure nutsche. The results obtained in regard to acid value, hydroxyl value and color standard number are shown in Table 6.

TABLE 6

Dependence of the product specifications where solvents are used

Starting product: trimethyl propane + 3 EO triacrylate in toluene
Acid value: 18 mg KOH/g
Hydroxyl value: 25 mg KOH/g
Gardner color standard number: below 1

Temperature: 80° C.
Pressure: 50 mbar

| | Neutralization time mins | Acid value mg KOH/g | Hydroxyl value mg KOH/g | Gardner color standard number |
|---|---|---|---|---|
| 36.9 g Ca(OH)$_2$ | 60 | 1.3 | 26 | below 1 |
| (2x equival.) | 120 | 0.5 | 26 | 2 |
| | 180 | 0.4 | 28 | 4 |
| 27.9 g CaO | 60 | 5.6 | 27 | below 1 |
| (2x equival.) | 120 | 4.0 | 27 | below 1 |
| | 180 | 2.7 | 28 | below 1 |
| Combination | | | | |
| 20.1 g MgO | 60 | 14.1 | 25 | below 1 |
| (2x equival., based on AV) | | | | |
| +28.9 g Ca(OH)$_2$ | 120 | 2.6 | 25 | below 1 |
| (1.5x equival., based on AV) | | | | |
| after 60 mins) | 180 | 0.5 | 26 | below 1 |
| Combination | | | | |
| 25.6 g hydrotalcite (2x | 60 | 9.7 | 25 | below 1 |
| equival., based on AV) | 120 | 2.6 | 25 | below 1 |
| +19.9 g Ca(OH)$_2$ | 180 | 1.1 | 26 | below 1 |
| (1.5x equival., based on AV after 60 mins) | | | | |

We claim:

1. A process for producing essentially neutral, low-volatility, reactive olefinic double bond containing organic compounds from a liquid mixture containing the reactive olefinic double bond containing compounds in admixture with lesser amounts of acid components, which comprises: contacting the liquid mixture comprising esters of polyfunctional alcohols and olefinically unsaturated carboxylic acids with at least one finely divided solid comprising at least one composition selected from the group consisting of alkali metal oxides, alkali metal hydroxides, alkali metal carbonates, alkaline earth metal oxides, alkaline earth metal hydroxides and alkaline earth metal carbonates, under substantially anhydrous conditions, at a temperature above 50° C. to form a neutralized organic liquid phase and a solid phase and separating the neutralizing organic liquid phase from the solid phase.

2. A process of claim 1, wherein the finely divided solid comprises at least one composition selected from the group consisting of calcium oxide, calcium hydroxide, magnesium oxide and magnesium hydroxide.

3. A process of claim 1, wherein the liquid mixture is contacted with the finely divided solid for less than 1 hour.

4. A process of claim 1 wherein the liquid mixture is contacted with the finely divided solid at a temperature in the range of from about 60° to 100° C. for from about 5 to 60 minutes.

5. A process of claim 1 wherein the liquid mixture is contacted with the finely divided solid at a pressure in the range of from about 1 to about 150 mbar.

6. A process of claim 1 wherein the neutralized organic liquid phase has an acid number below 1.5 mg KOH/g and a color number of less than 2 (determined according to Gardner).

7. A process of claim 1 wherein the liquid mixture comprises at least one substantially water-free polymerization or gelation-endangered, olefinically unsaturated organic compound containing residual acid from a condensation and acid catalyst.

8. A process of claim 1 wherein the finely divided solid comprises calcium oxide or hydroxide in a mixture with hydrotalcite.

9. A process of claim 1 wherein the finely divided solid is present in at least a stoichiometric amount to neutralize the acid components in the liquid mixture.

10. A process of claim 3 wherein the liquid mixture is contacted with the finely divided solid for not longer than 45 minutes.

11. A process of claim 4 wherein the temperature is in the range of from about 70° C. to about 90° C.

12. A process of claim 6 wherein the acid number is less than about 1 and the color number is less than about 1.

13. A process of claim 7 wherein the liquid mixture comprises an organic solvent.

14. A process of claim 1 wherein the liquid mixture comprises at least one ester of a polyfunctional alcohol with at least one carboxylic acid selected from the group consisting of acrylic acid nd methacrylic acid.

15. A process of claim 1 wherein the liquid mixture is contacted with the finely divided solid under a reduced pressure to reduce an amount of water in the neutralized organic liquid phase.

16. A process of claim 15 wherein the amount of water in the neutralized organic liquid phase is less than about 0.1% by weight of the neutralized organic liquid phase.

17. A process of claim 9 wherein the finely divided solid is present in an amount of from about 1.3 to about 2.5 times the stoichiometric amount required to neutralize the acid components in the liquid mixture.

* * * * *